(12) United States Patent
Sudo et al.

(10) Patent No.: US 8,586,785 B2
(45) Date of Patent: Nov. 19, 2013

(54) PROCESS FOR PRODUCING CATALYST FOR METHACRYLIC ACID PRODUCTION AND PROCESS FOR PRODUCING METHACRYLIC ACID

(75) Inventors: Atsushi Sudo, Takasaki (JP); Kazuo Shiraishi, Takasaki (JP); Hideki Sugi, Gunma (JP); Hiroyoshi Nowatari, Takasaki (JP); Fumio Sakai, Sanyoonoda (JP); Tomoaki Kobayashi, Sanyoonoda (JP); Tatsuhiko Kurakami, Sanyoonoda (JP)

(73) Assignee: NipponKayaku KabushikiKaisha, Tokyo (JP)

( * ) Notice: Subject to any disclaimer, the term of this patent is extended or adjusted under 35 U.S.C. 154(b) by 199 days.

(21) Appl. No.: 13/298,645

(22) Filed: Nov. 17, 2011

(65) Prior Publication Data

US 2012/0065427 A1     Mar. 15, 2012

Related U.S. Application Data

(63) Continuation-in-part of application No. PCT/JP2010/058869, filed on May 26, 2010.

(30) Foreign Application Priority Data

May 26, 2009    (JP) ................. 2009-126943

(51) Int. Cl.
  *C07C 51/16* (2006.01)
  *B01J 27/199* (2006.01)
  *B01J 27/19* (2006.01)

(52) U.S. Cl.
  USPC .............. 562/524; 562/535; 502/209

(58) Field of Classification Search
  USPC ............... 562/524, 535; 502/209, 211
  See application file for complete search history.

(56) References Cited

U.S. PATENT DOCUMENTS

| 4,564,607 A | 1/1986 | Yoneda et al. |
| 2009/0036707 A1* | 2/2009 | Sudo et al. ............ 562/524 |

FOREIGN PATENT DOCUMENTS

| JP | 58-51943 A | 3/1983 |
| JP | 2-36296 B2 | 8/1990 |
| JP | 2003-10691 A | 1/2003 |
| JP | 3797148 B2 | 7/2006 |

OTHER PUBLICATIONS

International Search Report mailed Aug. 31, 2010 in corresponding PCT application No. PCT/JP2010/058869.

* cited by examiner

*Primary Examiner* — Yong Chu
(74) *Attorney, Agent, or Firm* — Nields, Lemack & Frame, LLC

(57) ABSTRACT

An object of the present invention is to provide a process for stably producing a catalyst for methacrylic acid production exhibiting high activity and high performance. The process for producing a catalyst for methacrylic acid production of the invention is characterized in that the water content of the catalyst ingredient powder for use in molding, temperature and humidity of a molding step, humidity and temperature of a baking step are individually controlled in the case where molding is performed by a coating method using an Mo—V—P—Cu-based hetero polyacid as an active ingredient and water or an alcohol and/or an aqueous solution of an alcohol as a binder.

7 Claims, No Drawings

PROCESS FOR PRODUCING CATALYST FOR METHACRYLIC ACID PRODUCTION AND PROCESS FOR PRODUCING METHACRYLIC ACID

CROSS-REFERENCE TO RELATED APPLICATIONS

This is a Continuation-In-Part application of International patent application No. PCT/JP2010/058869 filed on May 26, 2010

TECHNICAL FIELD

The present invention relates to a process for producing a catalyst for methacrylic acid production for use in the production of methacrylic acid by vapor-phase catalytic oxidation of a raw material for methacrylic acid production, such as methacrolein, isobutyraldehyde, or isobutyric acid.

BACKGROUND ART

As catalysts to be used for producing methacrylic acid by vapor-phase catalytic oxidation of methacrolein, isobutyraldehyde, isobutyric acid, or the like, it is known that those having a structure of a hetero polyacid and/or a salt thereof are effective, and there are a large number of proposals regarding compositions, physical properties, and production processes thereof.

These catalysts are usually produced by steps of preparation of a raw material mixed solution, drying, molding, baking, and the like. With regard to the production of the catalysts stably exhibiting high performance, there are a large number of reports on molding methods and baking methods.

For example, in Patent Document 1, a process for molding with mixing heat-resistant fibers has been proposed for the purpose of enhancing the strength of the catalysts. Moreover, in Patent Document 2, in the production of a hetero polyacid salt-based catalyst, there has been proposed a process of treating a molded catalyst under a certain humidity atmosphere and subsequently performing baking.

BACKGROUND ART DOCUMENTS

Patent Documents

Patent Document 1: JP-B-2-36296
Patent Document 2: Japanese Patent No. 3797148

SUMMARY OF THE INVENTION

Problems that the Invention is to Solve

However, a catalyst including a hetero polyacid as an active ingredient has extremely high affinity to water or alcohols as compared with the hetero polyacid salt-based catalysts, and thus, for stably producing a high-performance catalyst, it is insufficient to perform only baking simply after a molded catalyst has been treated under a certain humidity atmosphere. Particularly, in the case where a hetero polyacid is used as an active ingredient and molding is performed by a coating method where the acid is supported on a support using water or an alcohol and/or an aqueous solution of an alcohol as a binder, it is difficult to produce a catalyst stably exhibiting high performance. Namely, since it is necessary to use a large amount of a binder owing to insufficient supporting in the coating step, catalyst ingredients are dissolved owing to dew condensation on a catalyst surface during the molding step or after molding to change surface conditions, or exfoliation or the like of the catalyst ingredients occurs depending on conditions at the drying and baking steps after molding, there often occurs a case where intrinsic catalytic performance is not exhibited, so that it is extremely difficult to produce an industrial catalyst.

An object of the present invention is to provide a process for producing a catalyst for methacrylic acid production stably exhibiting high activity and high performance, with overcoming these difficulties.

Means for Solving the Problems

As a result of the extensive studies, the present inventors have found that, in the case where an Mo—V—P—Cu-based hetero polyacid is used as an active ingredient and molding is performed by a coating method, it is possible to produce a catalyst for methacrylic acid production stably exhibiting high activity and high performance by controlling the water content of the catalyst powder for use in molding, the temperature and humidity of the molding step, the humidity and temperature of the baking step individually. Thus, they have accomplished the invention.

Thus, the present invention includes:

(1) A process for producing a catalyst for methacrylic acid production comprising coating a support with a catalyst ingredient powder comprising as an active ingredient a hetero polyacid containing molybdenum, phosphorus, vanadium, and copper and further baking the same, wherein the process comprises:

a catalyst molding step of using the catalyst ingredient powder having a water content of 8.0 to 10.0% by weight and coating a support with the catalyst ingredient powder under an atmosphere of an absolute humidity of 0.007 to 0.025 kg/kgDA, and a baking step of charging a catalyst molded in the catalyst molding step into a drying and baking apparatus under an atmosphere of an absolute humidity of 0.007 to 0.025 kg/kgDA and baking the catalyst by elevating the temperature within 30 minutes after charging to a temperature at which relative humidity reaches 10% or less.

(2) The process according to (1) above, wherein the catalyst ingredient powder having a water content of 8.0 to 10.0% by weight is obtained by drying an aqueous solution containing a compound containing ingredients of the catalyst or a water dispersion of the compound, with feeding humidified air.

(3) The process according to (1) above or (2) above, wherein, in the catalyst molding step, a binder is used together with the catalyst ingredient powder and at least one of water and an alcohol having a boiling point of 150° C. or lower under 1 atm is used as the binder.

(4) The process according to (3) above, wherein the alcohol is used as the binder and the concentration of methyl alcohol or ethyl alcohol in the alcohol is 70% by weight or more.

(5) The process according to (3) above or (4) above, wherein the binder contains ethyl alcohol.

(6) The process for producing a catalyst according to any one of (1) to (5) above, wherein the active ingredient of the catalyst for methacrylic acid production is represented by the general formula (I):

$$Mo_a P_b V_c Cu_d X_e O_f \qquad (I)$$

wherein Mo, P, V, and Cu represent elements of molybdenum, phosphorus, vanadium, and cupper, respectively; X represents one or more elements selected from arsenic, silver, zirconium, boron, germanium, tin, lead, chromium, bismuth, cobalt, nickel, cerium, tungsten, iron, aluminum, magnesium, antimony, and titanium; O represents an oxygen element; a subscript at lower right of the symbol of an element is an atomic ratio of each element and when a is 10, b is 0.1 or more and 6 or less, c is 0.3 or more and 6 or less, d is 0.01 or more and 5 or less, e is 5 or less including 0, and f is a numeric value determined depending on an oxidation state of each element.

(7) A process for producing methacrylic acid by vapor-phase catalytic oxidation of methacrolein, isobutyraldehyde, or isobutyric acid in the presence of the catalyst produced by the process according to any one of (1) to (6) above.

Outcome of the Invention

According to the production process of the invention, a high-activity and high-performance catalyst for methacrylic acid production including a hetero polyacid containing molybdenum, phosphorus, vanadium, and copper as an active ingredient can be stably produced by a coating method.

MODE FOR CARRYING OUT THE INVENTION

The production process comprises a step of preparing an aqueous solution containing a compound containing catalyst ingredients such as molybdenum, phosphorus, vanadium, and copper or a water dispersion of the compound (hereinafter collectively referred to as a slurry), a step of drying the slurry to obtain a powder, a step of molding by a coating method using the resulting powder, and a step of subsequent baking.

In the production process of the invention, compounds containing each of or plurality of Mo, V, P and Cu and, if necessary, the other elements are dissolved and/or dispersed in water to prepare a slurry and the resulting slurry is dried.

In the invention, as ingredients other than Mo, V, P and Cu, one or more kinds selected from As, Ag, Zr, B, Ge, Sn, Pb, Cr, Bi, Co, Ni, Ce, W, Fe, Al, Mg, Sb, and Ti are preferred, and As and Sb are particularly preferred.

As raw materials containing Mo, V, P and Cu and the above elements to be used according to needs, chlorides, sulfates, nitrates, oxides, acetates, or the like of the ingredient elements can be used. When preferable compounds are more specifically exemplified, there may be mentioned oxides such as molybdenum oxide, vanadium pentoxide, antimony trioxide, cerium oxide, zinc oxide, or germanium oxide; acids (or salts thereof) such as orthophosphoric acid, phosphoric acid, arsenic acid, boric acid, aluminum phosphate, or 12 tungstophosphoric acid, and the like. They may be used singly or two or more thereof may be used as a mixture.

Regarding the ratios of individual ingredients of the catalyst in the invention, as atomic ratios, phosphorus is 0.1 or more and 6 or less, preferably 0.3 or more and 4 or less, vanadium is 0.3 or more and 6 or less, preferably 0.5 or more and 2 or less, cupper is 0.01 or more and 5 or less, preferably 0.1 or more and 3 or less relative to molybdenum that is 10. The kinds and use ratios of the other ingredients to be used according to needs are appropriately determined so that a catalyst exhibiting optimum performance is obtained according to use conditions of the catalyst and the like. A preferable catalyst to be used in usual conditions is one having an active ingredient composition represented by the following formula (I):

$$Mo_a P_b V_c Cu_d X_e O_f \qquad (I)$$

wherein Mo, P, V, and Cu represent elements of molybdenum, phosphorus, vanadium, and cupper, respectively; X represents one or more elements selected from arsenic, silver, zirconium, boron, germanium, tin, lead, chromium, bismuth, cobalt, nickel, cerium, tungsten, iron, aluminum, magnesium, antimony, and titanium; O represents an oxygen element; a subscript at lower right of the symbol of an element is an atomic ratio of each element and when a is 10, b is 0.1 or more and 6 or less, c is 0.3 or more and 6 or less, d is 0.01 or more and 5 or less, e is 5 or less including 0, and f is a numeric value determined depending on an oxidation state of each element. As the composition ratio of the general formula (I), more preferably, when a is 10, b is 0.3 or more and 4 or less, c is 0.5 or more and 2 or less, d is 0.1 or more and 3 or less, e is 0.1 or more and 3 or less, and f is a numeric value determined depending on an oxidation state of each element.

In the invention, the use ratio of the compound of each ingredient in the preparation of the slurry may be determined so that the atomic ratio of each ingredient becomes a prescribed ratio, preferably falls within the range mentioned above. The amount of water to be used is not particularly limited so long as it is an amount with which the total amount of the compounds to be used can be completely dissolved or can be homogeneously mixed (dispersed) but is appropriately determined in consideration of the drying method, drying conditions, and the like to be mentioned below. For example, usually, based on 100 parts by weight of the total of the compounds for slurry preparation, about 200 to 2,000 parts by weight of water is used. The amount of water may be a large amount but when the amount is too large, it becomes difficult to control the particle size of the catalyst ingredient powder after drying to a prescribed range and also there are many demerits such that an energy cost for the drying step increases, drying takes much time, and the like, so that it is preferred to use an appropriate amount.

Then, the slurry obtained in the above is dried to form the catalyst ingredient powder. The drying method is not particularly limited so long as it is a method capable of controlling the water content of the powder after drying to the prescribed range. For example, drum drying, freeze drying, spray drying, and the like may be mentioned. Of these, in the invention, the spray drying capable of drying from a slurry state to a powder or granules for a short period of time is preferred. The drying temperature in this case varies depending on the concentration of the slurry, solution-transferring rate, and the like but the outlet temperature of a drier is generally 85 to 130° C. On this occasion, drying is preferably performed so that the average particle size of the resulting catalyst ingredient powder becomes 30 to 150 μm. In the case where the catalyst ingredient powder is clumpy or in a large particle form, it is preferred to form particles having the above particle size by proper pulverization or the like. In the invention, the catalyst ingredient powder also includes one thus pulverized.

As a method of controlling the water content in the catalyst ingredient powder to the prescribed range, methods of controlling inlet and outlet temperature of the drier, drying time, humidity of the drying atmosphere, and the like and a method of variously combining the above methods may be mentioned. Of these, the method of drying under an atmosphere where humidity is controlled affords good homogeneity of the water content in the resulting catalyst ingredient powder and is easy to control. In the case of a spray drier, the water content of the catalyst ingredient powder can be controlled by controlling the amount of water in the air to be introduced into the spray drier and adjusting the spray drying rate and the outlet temperature of the spray drier. Although a suitable amount of water in the air to be introduced into the spray drier or the like varies depending on the drying conditions, in the usual cases, it is preferred to use an air containing such an amount of water that a dew point is 15° C. or higher, for example, by a method of feeding an air humidified using a humidifier.

A hetero polyacid contains crystal water in the crystal structure. When the amount of the crystal water changes, the surface area changes and the affinity to a binder ingredient such as water or an alcohol changes. Therefore, the use in the molding step with controlling the water content in the catalyst ingredient powder to a prescribed range is extremely important for stable production of a high-performance catalyst. The water content of the catalyst ingredient powder to be used in the molding step is suitably 8.0 to 10.0% by weight. When the water content of the catalyst ingredient powder itself is lower than the prescribed range, the catalyst ingredient powder is difficult to support on a support. When the amount of the catalyst ingredient powder to be supported decreases, there occur inconveniences such as a decrease in catalytic activity. When a large amount of a binder is used for supporting the catalyst ingredient powder having a low water content, there occur inconveniences that the powder is prone to attach on the wall surface of a coating apparatus to decrease the amount thereof supported on the support, exfoliation of the catalyst ingredients supported in the baking step of the molded article is prone to occur, and so forth, so that the case is not preferred. On the other hand, when the water content is higher than the prescribed range, homogeneous supporting on the support is not achieved or there tends to occur inconveniences that the coating catalyst ingredients are exfoliated from the support in the baking step and so forth, so that the case is not preferred.

The method of measuring the water content in the catalyst ingredient powder is as follows. The catalyst ingredient powder after measured (power before heating) is placed in a crucible and it is placed in an electric oven where the oven temperature is set to 400° C. After 2 hours, the crucible is taken out and the catalyst ingredient powder in the crucible is measured. Then, the water content is calculated by the following calculation method.

Water content (% by weight)=100×(Powder weight before heating−Powder weight after heating)/ Powder weight before heating In the molding by the coating method, in order to improve workability, molding can be performed after mixing with a molding aid such as silica gel, diatomaceous earth, alumina powder, crystalline cellulose powder, or starch powder. In the case where the molding aid is used, suitably, the amount is usually 1 to 30 parts by weight based on 100 parts by weight of the catalyst ingredient powder. Moreover, it is useful for enhancing mechanical strength of the catalyst to use further inorganic fibers inactive to the catalyst ingredients, such as ceramic fibers or whiskers, as a strength enhancer according needs. Suitably, the amount of the fibers to be used is usually 1 to 30 parts by weight based on 100 parts by weight of the catalyst ingredient powder. However, of inorganic fibers, fibers reactive with the hetero polyacid, such as potassium titanate whiskers or basic magnesium carbonate whiskers, are not preferred. Since these molding aid and strength enhancer are preferably dispersed homogeneously prior to the coating of the support, it is preferred to use them in the molding step with homogeneously mixing them with the catalyst ingredient powder beforehand.

The catalyst ingredient powder obtained as above or the mixture obtained by mixing the powder with the molding aid and the strength enhancer is molded into a molded article having a size of about 3 to 15 mm in order to reduce pressure loss of a reactive gas, and the molded article is packed into a reaction tube of a fixed bed reactor and used for the methacrylic acid production reaction. As the molding method, various methods such as tableting molding, extrusion molding, marumerizing molding are considered. However, with a catalyst molded by a method of coating the support with the catalyst ingredient powder or the mixture with the molding aid and/or the strength enhancer, an improvement in selectivity and an improvement in efficiency of removing reaction heat can be expected. For the coating, usual coating methods can be used but a rolling granulation method described below is preferred.

The method is a method of coating a support with a supporting powder where, in an apparatus having a flat or uneven disk at the bottom of a fixed container, the support in the container is stirred through repetition of autorotation movement and orbital movement by rotating the disk at a high speed and a binder and a catalyst powder or a mixture with a molding aid and/or a strength enhancer (hereinafter described as a "supporting powder") is added thereto. The method of adding the binder and the supporting powder is not particularly limited. For example, methods of 1) mixing the binder and the supporting powder beforehand, 2) adding them at the time when they are added into the fixed container, 3) adding the binder after the supporting powder is added into the fixed container, 4) adding the supporting powder after the binder is added into the fixed container, 5) dividing each of the supporting powder and the binder and adding all amount of them with appropriately combining 2) to 4), and the like may be arbitrarily adopted. As methods of adding them, it is preferred to perform the addition with regulating addition rates using a metering pump for the binder and an auto feeder or the like for the supporting powder.

As the binder, at least one selected from the group consisting of water and alcohols having a boiling point of 150° C. or lower under 1 atm can be used. Since it is necessary to remove most of the binder during the drying and baking steps after coating, one having not so high boiling point is preferred. Specific examples of the alcohols include alcohols such as methanol, ethanol, propanols, and butanols but, of these, ethanol is preferred. As the alcohols, in addition to alcohols containing no organic compound other than the alcohols, those to which another kind of alcohol or a small amount of an organic compound is added (mixed alcohols) are also usable. However, from the viewpoint of removing the alcohol used as the binder, it is preferred that the concentration of an alcohol having a boiling point of 150° C. or lower under 1 atm is 70% by weight or more.

As the binder, in addition to the alcohols, water can be also used but, from the viewpoint of operability in the molding step, it is preferred to use an aqueous alcohol solution. For example, in the case where ethanol is used as the binder, an aqueous ethanol solution having any concentration can be used but the ethanol concentration is preferably 10% by weight or more. The amount of these binders to be used is usually 10 to 60 parts by weight, preferably 15 to 40 parts by weight based on 100 parts by weight of the supporting powder.

Specific examples of the support usable in the invention include silicon carbide, alumina, silica-alumina, mullite, and the like. The diameter of the support is 1 to 15 mm, preferably 2.5 to 10 mm and a spherical support may be mentioned. As these supports, those having a porosity of 10 to 70% are usually employed. Regarding the ratio of the support to the supporting powder, there are used amounts so that supporting powder/(supporting powder+support) is usually 10 to 75/100, preferably 15 to 60/100 as a weight ratio.

Thus, the support is coated with the supporting powder and the molded article obtained on this occasion usually has a diameter of about 3 to 15 mm.

As mentioned above, since the hetero polyacid has high affinity to water or alcohols, catalytic performance remarkably changes depending on the temperature in the molding step and the humidity in the air, so that it is extremely important for stably producing high-performance catalyst to control the temperature and humidity to prescribed ranges also in the molding step. Since these conditions influence the catalytic performance to a large extent even in the vicinity of ordinary temperature and in the range of usual humidity in the air, when molding is performed without controlling these conditions, stable production of the high-performance catalyst cannot be achieved. In the invention, the atmosphere of the apparatus and peripheral instruments for carrying out the molding step may be usually 15 to 35° C. and an absolute humidity of 0.007 to 0.025 kg/kgDA, while the temperature is not particularly limited to these ranges. From the viewpoint of workability and costs required for temperature and humidity adjustment, a temperature of 20 to 30° C. is preferred. Moreover, since there is a concern that dew condensation on the apparatus surface and molded article surface may occur by slight temperature change when relative humidity in the air increases, an absolute humidity of 0.007 to 0.021 kg/kgDA and relative humidity of 99% or less at a temperature of 20 to 30° C. are preferred.

In the case where molding is performed by the method of the invention, since interaction between the molded article and air atmosphere depends on the amount of water contained in the air, a suitable humidity range should be controlled by not relative humidity that is commonly used but absolute humidity. As a matter of course, the absolute humidity can be converted into the relative humidity but, since saturated vapor pressure increases with temperature, the relative humidity decreases with the elevation of temperature even when the absolute humidity is the same. The absolute humidity described in the invention is, relative to 1 kg of dry air weight excluding water vapor in the atmosphere, weight (kg) of the excluded water vapor. When the absolute humidity of the apparatus and peripheral instruments for carrying out the molding step is lower than the aforementioned range, the catalyst ingredient powder becomes difficult to support on the support and the amount of the catalyst ingredient powder to be supported on the support decreases, so that there occur inconveniences such as a decrease in catalytic activity. For supporting the support with a prescribed amount of the catalyst ingredient powder under a condition where the absolute humidity is lower than the aforementioned range, it is necessary to use a large amount of a binder. When a large amount of the binder is used, there occur inconveniences that a powder is prone to attach on the wall surface of the coating apparatus and thus the amount of the catalyst ingredient powder to be used also increases, so that the case is not preferred. Furthermore, since the molded article thus produced contains a large amount of the binder, there occurs inconveniences that exfoliation of the catalyst ingredients supported in the baking step is prone to occur and so forth, so that the case is not preferred. On the other hand, when the absolute humidity is higher than the prescribed range, the powder and the molded article are prone to attach in the apparatus and there tends to occur inconveniences such as a decrease in supported amount on the support and a decrease in productivity, an increase in the amount of the catalyst ingredient powder used, and facility breakdown.

The temperature control in the molding step can be performed by a usual temperature-controlling instrument and, for the humidity control, a usual humidifier or dehumidifier can be used but it is necessary to have a sufficient capacity in comparison to the room volume of the apparatus and peripheral instruments for carrying out the molding step.

For converting the molded article molded by the process of the invention into a catalyst usable in reactions, it is necessary to perform subsequent drying and baking. In these steps, most of the binder used for molding, such as water or an alcohol, is removed, which is necessary to form an industrial catalyst having a sufficient strength or suitable physical properties for practical use. Also, in the case of using the catalyst in the reaction for methacrylic acid production, it is a necessary step for not causing unnecessary heat generation and by-product formation.

The molded article molded by the coating method in the above molding step should be placed promptly under a certain atmosphere. As atmospheric conditions for storing the molded article, temperature and humidity are important. For example, when it is stored under a high-humidity atmosphere, there is a concern that water in the air acts on the surface of the molded article to dissolve the catalyst active ingredients on the surface. Moreover, in the case where humidity is extremely low, there is a concern that the supporting powder is prone to exfoliate from the support owing to rapid vaporization of water or the alcohol in the molded article and the catalyst strength decreases.

Furthermore, in the case of high temperature, since the binder such as water or an alcohol is rapidly vaporized, the supporting powder is prone to exfoliate from the support and the catalyst strength decreases, and in an extreme case, the supporting powder exfoliates from the support. In the case where a binder containing an organic compound such as an alcohol is used, when the temperature is high, the organic compound contained in the molded article is rapidly vaporized and there is a possibility that the surrounding atmosphere becomes a condition of explosion range, so that care should be taken. On the other hand, in the case of low temperature, a binder such as an alcohol takes away heat of vaporization when it vaporizes and the temperature on the molded article surface lowers, so that there is a concern that dew condensation occurs on the molded article surface to dissolve the catalyst active ingredients on the surface. For the above reasons, it is better to place the molded article in a dry chamber or drying apparatus within 25 minutes at latest, preferably within 10 minutes after the finish of the molding step.

The dry chamber or drying apparatus to be used in the invention is not particularly limited but, since it is necessary to control humidity in addition to temperature, not an opened type but a closed type where part of the inner air is circulated is preferred. Moreover, although baking may be performed in another apparatus after drying, it is convenient to use the same apparatus for baking and drying since atmosphere adjustment is not necessary at the transfer of the molded article after drying.

In the case where the molded catalyst is dried and baked, when it is rapidly charged into a high temperature atmosphere or a low humidity atmosphere, there arise inconveniences such as exfoliation and dissolution of the catalyst ingredients owing to rapid vaporization of the binder used in the molding. Thus, as the conditions for charging the molded article into the drying and baking apparatus, a temperature of 15 to 90° C. and an absolute humidity of 0.007 to 0.025 kg/kgDA are suitable and it is preferred to charge it under an atmosphere of a temperature of 30 to 75° C., an absolute humidity of 0.007 to 0.021 kg/kgDA, and a relative humidity of 99% or less in the temperature range, while the temperature is not particularly limited to these ranges. After charging into the apparatus, the whole is kept for 5 to 20 minutes until the temperature and humidity of the molded article and the drying and baking apparatus are stabilized and then the temperature is elevated within 30 minutes after charging to a temperature at which the relative humidity reaches 10% or less. The time for keeping under the conditions after charging into the drying and baking apparatus is sufficiently usually about 5 to 15 minutes. Since there is a concern that the vaporized binder and water vapor act on the catalyst surface when the catalyst is kept for an exceedingly long time, it is preferred to elevate the temperature within 25 minutes after charging to a temperature at which the relative humidity reaches 10% or less.

Incidentally, for the measurement of the absolute humidity and relative humidity, for example, a Neosensor indoor-type temperature/humidity sensor (Model Nos. TY7043 and HY7043) manufactured by Yamatake Corporation and a temperature/humidity meter (Model No. HMT361) manufactured by VAISALA can be employed.

In the baking step to be carried out after drying, as mentioned above, water and organic compounds such as alcohols used as binders at molding are removed by vaporization or oxidative decomposition. Since the alcohols form a certain kind of ester bond with the hetero polyacid, it is necessary to heat the catalyst to 150° C. or higher, preferably 170° C. or higher for removing the alcohols. Moreover, in the case where organic compounds are used as the molding aid, it is preferred to set the baking temperature so that these organic compounds are removed through sufficient oxidative decomposition. For example, in the case where starch powder is used as the molding aid, it is preferred to perform baking at a temperature of 330° C. or higher. On the other hand, since the hetero polyacid has a property that it is decomposed under a high-temperature condition, it is necessary to elevate the temperature of the baking apparatus gradually so that the temperature of the molded article is not exceedingly elevated by the heat of reaction of alcohol oxidation or the oxidation reaction of the organic compounds in the course of heating. Baking is usually performed at a temperature of 420° C. or lower but it is preferred to perform it at 380° C. or lower.

EXAMPLES

The following will describe the invention in further detail with reference to Examples. Incidentally, the invention is not limited to the following Examples unless it exceeds the gist. Moreover, part(s) in Examples and Comparative Examples means part(s) by weight and % means % by weight. Methacrolein conversion, methacrylic acid yield, and methacrylic acid selectivity are defined by percentages calculated in terms of mole as shown in the following expressions (2), (3), and (4), respectively. In this regard, the reaction products were qualitatively and quantitatively determined by gas chromatography.

Methacrolein conversion (%)=100×(Number of moles of reacted methacrolein)/(Number of moles of fed methacrolein) (2)

Methacrylic acid selectivity (%)=100×(Number of moles of formed methacrylic acid)/(Number of moles of reacted methacrolein) (3)

Methacrylic acid yield (%)=100×(Number of moles of formed methacrylic acid)/(Number of moles of fed methacrolein) (4)

Example 1

Into 7,100 ml of pure water were charged 1,000 g of molybdenum trioxide, 44.23 g of vanadium pentoxide, 88.11 g of an aqueous orthophosphoric acid solution having a concentration of 85%, and 82.18 g of an aqueous arsenic acid solution having a concentration of 60%, and the whole was stirred and heated at 92° C. for 3 hours to prepare a slurry. Thereafter, the slurry was spray-dried with introducing an air controlled to a relative humidity of 80.0% at 25° C. to obtain a catalyst powder having the following composition. The outlet temperature of the spray drier was 100 to 110° C., the medium value of particle size of the resulting catalyst powder was 75 μm, and the water content was 9.1%.

The composition was $Mo_{10}P_{1.1}V_{0.7}Cu_{0.2}As_{0.5}$ (the oxygen content varies depending on oxidation states and thus cannot be specified).

Then, 320 g of the granules and 55 g of a strength enhancer made of ceramic fibers were homogeneously mixed, and the mixture was molded using 300 g of a spherical porous alumina support (average particle size: 3.5 mm), using 75 g of an aqueous ethanol solution having a concentration of 90% as a binder, and using a rolling granulator set up in a room having a temperature of 23° C. and an absolute humidity of 0.015 kg/kgDA.

Thereafter, the resulting molded article was charged into a baking oven having an oven temperature of 50° C. and an absolute humidity of 0.016 kg/kgDA and, after kept for 12 minutes from charging, the temperature was elevated to 70° C. over a period of 12 minutes (relative humidity at 70° C.: 8.2%). Thereafter, the temperature was gradually elevated and the molded article was baked at 330° C. for 5 hours under an air stream to obtain a catalyst for methacrylic acid production.

Into a stainless steel reaction tube having an inner diameter of 18.4 mm was packed 10 ml of the resulting catalyst, and an oxidation reaction of methacrolein was carried out at a raw material gas composition (molar ratio) of methacrolein:oxygen:water vapor:nitrogen=1:2:4:18.6, a space velocity (SV) of 1,200 $hr^{-1}$, and a reaction bath temperature of 310° C. The reaction was first continued at a reaction bath temperature of 310° C. for 3 hours, then the temperature was elevated to 350° C., and the reaction was continued for 15 hours (hereinafter, the treatment is referred to as high-temperature reaction treatment). Then, the reaction bath temperature was lowered to 310° C. and measurement of reaction performance was conducted. When the oxidation reaction of methacrolein was carried out under a condition of a reaction temperature of 310° C., methacrolein conversion was 81.5%, methacrylic acid selectivity was 82.1%, and methacrylic acid yield was 66.9%.

Example 2

The slurry formulated in Example 1 was spray-dried with introducing an air adjusted to a relative humidity of 72.0% at 25° C. to obtain a catalyst powder having the following composition. The outlet temperature of the spray drier was 100 to 110° C., the medium value of particle size of the resulting catalyst powder was 75 μm, and the water content was 8.6%. The composition was $Mo_{10}P_{1.1}V_{0.7}Cu_{0.2}As_{0.5}$ (the oxygen content varies depending on oxidation states and thus cannot be specified).

Then, 320 g of the granules and 55 g of a strength enhancer made of ceramic fibers were homogeneously mixed, and the mixture was molded using 300 g of a spherical porous alumina support (average particle size: 3.5 mm), using 75 g of an aqueous ethanol solution having a concentration of 90% as a binder, and using a rolling granulator set up in a room having a temperature of 29° C. and an absolute humidity of 0.020 kg/kgDA.

Thereafter, the resulting molded article was charged into a baking oven having an oven temperature of 50° C. and an absolute humidity of 0.016 kg/kgDA and, after kept for 10 minutes from charging, the temperature was elevated to 70° C. over a period of 12 minutes (relative humidity at 70° C.: 8.2%). Thereafter, the temperature was gradually elevated and the molded article was baked at 330° C. for 5 hours under an air stream to obtain a catalyst for methacrylic acid production. With regard to the reaction performance of the resulting catalyst, methacrolein conversion was 82.9%, methacrylic acid selectivity was 79.9%, and methacrylic acid yield was 66.2%.

Comparative Example 1

The slurry formulated in Example 1 was spray-dried with introducing an air controlled to a relative humidity of 20.0% at 15° C. to obtain a catalyst powder having the following composition. The outlet temperature of the spray drier was 100 to 110° C., the medium value of particle size of the resulting catalyst powder was 75 μm, and the water content was 7.5%. The composition was $Mo_{10}P_{1.1}V_{1.2}Cu_{0.2}As_{0.3}$ (the oxygen content varies depending on oxidation states and thus cannot be specified).

The resulting catalyst powder was subjected to molding and baking as in Example 2 to obtain a catalyst for methacrylic acid production. With regard to the reaction performance of the resulting catalyst, methacrolein conversion was 76.8%, methacrylic acid selectivity was 83.2%, and methacrylic acid yield was 63.9%.

Example 3

A catalyst for methacrylic acid production was obtained by the production under the same setting conditions as in Example 2 except that the room temperature and the absolute humidity of the rolling granulator for molding were changed to 27° C. and 0.018 kg/kgDA (relative humidity: 79.0%) and the temperature and the absolute humidity at the charging of the molded article into the baking oven were changed to an oven temperature of 50° C. and an absolute humidity of 0.015 kg/kgDA. With regard to the reaction performance of the resulting catalyst, methacrolein conversion was 81.6%, methacrylic acid selectivity was 81.6%, and methacrylic acid yield was 66.6%.

Comparative Example 2

A catalyst for methacrylic acid production was obtained by the production under the same setting conditions as in Example 2 except that the room temperature and the absolute humidity of the rolling granulator for molding were changed to 16° C. and 0.0055 kg/kgDA and the temperature and the absolute humidity at the charging of the molded article into the baking oven were changed to an oven temperature of 50° C. and an absolute humidity of 0.017 kg/kgDA. With regard to the reaction performance of the resulting catalyst, methacrolein conversion was 74.4%, methacrylic acid selectivity was 82.9%, and methacrylic acid yield was 61.7%.

Example 4

A catalyst for methacrylic acid production was obtained by the production under the same setting conditions as in Example 3 except that the temperature and the absolute humidity at the charging of the molded article into the drying and baking oven were changed to 50° C. and 0.013 kg/kgDA. With regard to the reaction performance of the resulting catalyst, methacrolein conversion was 81.7%, methacrylic acid selectivity was 79.8%, and methacrylic acid yield was 65.3%.

The production conditions and results of the performance tests of Examples and Comparative Examples are collectively described in the following Table.

TABLE 1

| | Water content | Molding chamber | | Baking oven | | Metha-crolein coversion | Metha-crylic acid selectivity | Metha-crylic acid yield |
| --- | --- | --- | --- | --- | --- | --- | --- | --- |
| | | Temperature | Absolute humidity | Temperature | Absolute humidity | | | |
| Example 1 | 9.1 | 23 | 0.0150 | 50 | 0.016 | 81.5 | 82.1 | 66.9 |
| Example 2 | 8.6 | 29 | 0.0200 | 50 | 0.016 | 82.9 | 79.9 | 66.2 |
| Comparative Example 1 | 7.5 | 29 | 0.0200 | 50 | 0.016 | 76.8 | 83.2 | 63.9 |
| Example 3 | 8.6 | 27 | 0.0180 | 50 | 0.015 | 81.6 | 81.6 | 66.6 |
| Comparative Example 2 | 8.6 | 16 | 0.0055 | 50 | 0.017 | 74.4 | 82.9 | 61.7 |
| Example 4 | 8.6 | 27 | 0.0180 | 50 | 0.013 | 81.7 | 79.8 | 65.3 |

Units are as follows: water content: wt %, temperature: ° C., absolute humidity: kg/kgDA, conversion/selectivity/yield: %

While the invention has been described in detail and with reference to specific embodiments thereof, it will be apparent to one skilled in the art that various changes and modifications can be made therein without departing from the spirit and scope thereof.

The present application is based on Japanese Patent Application No. 2009-126943 filed on May 26, 2009 and an International patent application No. PCT/JP2010/058869 filed on May 26, 2010, and the entire contents thereof are incorporated herein by reference. Also, all the references cited herein are incorporated as a whole.

INDUSTRIAL APPLICABILITY

The catalyst produced by the present invention can be used in the production of methacrylic acid through vapor-phase catalytic oxidation of a raw material for methacrylic acid production, such as methacrolein, isobutyraldehyde, or isobutyric acid, by a multitubular fixed bed reaction apparatus.

What is claimed is:

1. A process for producing a catalyst for methacrylic acid production comprising coating a support with a catalyst ingredient powder comprising as an active ingredient a hetero polyacid containing molybdenum, phosphorus, vanadium, and copper and further baking the same, wherein the process comprises:

a catalyst molding step of using the catalyst ingredient powder having a water content of 8.0 to 10.0% by weight and coating a support with the catalyst ingredient powder under an atmosphere of an absolute humidity of 0.007 to 0.025 kg/kgDA, and a baking step of charging a catalyst molded in the catalyst molding step into a drying and baking apparatus under an atmosphere an absolute humidity of 0.007 to 0.025 kg/kgDA and baking the catalyst by elevating the temperature within 30 minutes after charging to a temperature at which relative humidity reaches 10% or less.

2. The process according to claim 1, wherein the catalyst ingredient powder having a water content of 8.0 to 10.0% by weight is obtained by drying an aqueous solution containing a compound containing ingredients of the catalyst or a water dispersion of the compound, with feeding humidified air.

3. The process according to claim 1 or 2, wherein, in the catalyst molding step, a binder is used together with the catalyst ingredient powder and at least one of water and an alcohol having a boiling point of 150° C. or lower under 1 atm is used as the binder.

4. The process according to claim 3, wherein the alcohol is used as the binder and the concentration of methyl alcohol or ethyl alcohol in the alcohol is 70% by weight or more.

5. The process according to claim 3, wherein the binder contains ethyl alcohol.

6. The process for producing a catalyst according to claim 1 or 2, wherein the active ingredient of the catalyst for methacrylic acid production is represented by the general formula (I):

$$Mo_aP_bV_cCu_dX_eO_f \qquad (I)$$

wherein Mo, P, V, and Cu represent elements of molybdenum, phosphorus, vanadium, and cupper, respectively; X represents one or more elements selected from arsenic, silver, zirconium, boron, germanium, tin, lead, chromium, bismuth, cobalt, nickel, cerium, tungsten, iron, aluminum, magnesium, antimony, and titanium; O represents an oxygen element; a subscript at lower right of the symbol of an element is an atomic ratio of each element and when a is 10, b is 0.1 or more and 6 or less, c is 0.3 or more and 6 or less, d is 0.01 or more and 5 or less, e is 5 or less including 0, and f is a numeric value determined depending on an oxidation state of each element.

7. A process for producing methacrylic acid by vapor-phase catalytic oxidation of methacrolein, isobutyraldehyde, or isobutyric acid in the presence of the catalyst produced by the process according to any one of claims 1 or 2.

* * * * *